(12) United States Patent
Bjerregaard

(10) Patent No.: US 8,556,873 B2
(45) Date of Patent: Oct. 15, 2013

(54) DRAINAGE VALVE AND COLLECTION BAG ASSEMBLY COMPRISING SAID VALVE

(75) Inventor: Henrik Bork Bjerregaard, Bronshoj (DK)

(73) Assignee: MBH-International A/S, Allerød (DK)

( * ) Notice: Subject to any disclaimer, the term of this patent is extended or adjusted under 35 U.S.C. 154(b) by 0 days.

(21) Appl. No.: 13/516,679

(22) PCT Filed: Jan. 28, 2011

(86) PCT No.: PCT/DK2011/050021
§ 371 (c)(1),
(2), (4) Date: Jun. 15, 2012

(87) PCT Pub. No.: WO2011/091798
PCT Pub. Date: Aug. 4, 2011

(65) Prior Publication Data
US 2012/0259300 A1 Oct. 11, 2012

(30) Foreign Application Priority Data
Jan. 29, 2010 (DK) ................................ 2010 00075

(51) Int. Cl.
*A61F 5/44* (2006.01)
*A61M 1/00* (2006.01)
*F16K 5/04* (2006.01)
*F16K 5/12* (2006.01)
*F16K 5/18* (2006.01)

(52) U.S. Cl.
USPC ............ 604/327; 604/335; 604/540; 604/544

(58) Field of Classification Search
USPC .......... 604/316, 544, 540; 251/304, 309, 311, 251/315.01, 315.07, 314, 231, 248, 205, 251/206, 207, 208, 209
See application file for complete search history.

(56) References Cited

U.S. PATENT DOCUMENTS 4,540,156 A * 9/1985 Cross ............................ 251/309
4,844,415 A   7/1989 Nielsen et al. ................. 251/325
4,904,245 A * 2/1990 Chen et al. .................... 604/248
(Continued)

FOREIGN PATENT DOCUMENTS

EP    0 953 322 A2   11/1999
EP    1 623 688 A1   2/2006
WO    WO 2006/025054 A2   3/2006

OTHER PUBLICATIONS

International Search Report, PCT/DK2011/050021, mailed May 17, 2011.

*Primary Examiner* — Adam Marcetich
(74) *Attorney, Agent, or Firm* — Winston & Strawn LLP

(57) ABSTRACT

A drainage valve that has an inlet and outlet openings extending in opposite directions from a valve housing, a movable valve member within the housing and an operating lever connected to the valve member. The valve member is movable between an open position in which the valve member is arranged to permit flow through the valve and a closed position where the valve member prevents flow through the valve. The valve member is configured such that the valve member is moved from the closed position to an open position by rotating the operating lever by a first rotating angle between about 2 degrees to about 80 degrees. This provides a simple and inexpensive drainage valve, where patients having an extremely limited dexterity will only need to rotate the operating lever a few degrees before a flow path is such that drainage can begin.

16 Claims, 7 Drawing Sheets

(56) References Cited

U.S. PATENT DOCUMENTS

| | | | |
|---|---|---|---|
| 5,005,604 A * | 4/1991 | Aslanian | 137/556 |
| 5,113,904 A * | 5/1992 | Aslanian | 137/556 |
| 5,156,186 A * | 10/1992 | Manska | 137/556 |
| 5,275,373 A * | 1/1994 | Kalippke et al. | 251/208 |
| 5,443,453 A * | 8/1995 | Walker et al. | 604/248 |
| 5,476,246 A * | 12/1995 | Wendel et al. | 251/129.11 |
| 5,496,010 A * | 3/1996 | Collyer | 251/78 |
| 2004/0021115 A1 * | 2/2004 | Lemmonier et al. | 251/207 |
| 2006/0033066 A1 * | 2/2006 | Carrez et al. | 251/297 |
| 2007/0287953 A1 | 12/2007 | Ziv et al. | 604/31 |

* cited by examiner

DRAINAGE VALVE AND COLLECTION BAG ASSEMBLY COMPRISING SAID VALVE

This application is a 371 filing of International Patent Application PCT/DK2011/050021 filed Jan. 28, 2011.

BACKGROUND

The present invention relates to a drainage valve comprising an inlet opening and an outlet opening extending in opposite directions from a valve housing, a movable valve member within the housing and an operating lever connected to the valve member, said valve member is movable between an open position in which the valve member is arranged to permit flow through the valve and a closed position where the valve member prevents flow through the valve. The invention further relates to a collection bag assembly comprising said valve.

A large number of people have medical problems that cause bladder incontinence either on a temporary or permanent basis. In order for such persons to have a reasonably normal life, they are fitted with catheters for collection bag which normally is strapped to the person's leg during the day. Alternatively said bag can be placed beside a bed during the night e.g. connected to a larger storage bag.

Such known urine collection assemblies have a variety of problems that range from annoyance and embarrassment to actual health hazard.

One of these problems is that when the bag fills with urine it becomes heavy and uncomfortable, which can restrict the patient socially and cause anxiety and embarrassment. It is therefore necessary to have a drainage valve attached to the collection bag. This ensures that the patient or user conveniently can empty the bag during the daytime and use the valve as a connection point to a larger storage bag for overnight use. In the latter situation the valve remains open.

The valve is normally connected to the bag by a length of tubing close to the person's body, and drainage valves used in the conventional collection system, comprises an operation lever, which is movable between a closed position generally parallel to the length of tubing and an open position generally at right angles thereto. In the open position the projecting lever may press into the person's body and may be inadvertently moved to the closed position for example when the person turns over in his sleep.

Such a valve is e.g described in GB 2129912, where the operating lever moves through an angle of substantially 90 degrees between the valve-open and valve-closed positions. However when the valve is in the open position the operating lever will protrude perpendicular from the valve. This means that for applications where it may be necessary to leave the valve in the open position for longer periods, for example in drainage systems connected to bedside storage bags and especially in systems for overnight use and for bedridden patients, the protruding lever presents increased risks of snagging the bedclothes causing inadvertent closure of the valve or of providing discomfort to the patient.

In order to meet this problem both GB 2269884 and EP 428 331 describes drainage valve having an operating lever that lies substantially parallel with the tubes connected to the valve in both the open and closed position. However, since these valves will not be placed in an open position before the operating lever has been placed parallel to the opposite tubes, these valves has the significant drawback that patients having a limited manual dexterity find it difficult to apply the amount of stress needed to rotate the lever between the two positions, i.e. rotating the lever more than 150 degrees, several times during the day when the valve is opened for periodic drainage. Consequently, the users often experience difficulty in opening or closing the valve or have to use two hands to operate the valve.

Furthermore, it is not always obvious to the user whether the valve is open or closed, leading to the risk of leakage if the valve is inadvertently left open.

Electrically controlled and operated valves have also been used in the prior art urine bag systems. But, their use presents other problems. First, such valves require a power source, which not only is expensive to maintain but also provides the risk of failing at very inconvenient times, leaving the valve in the open or closed position. Stuck in the open position, the valve will not close the urine bag leading to contamination of the surroundings, and stuck in the closed position, the valve will not allow the drainage system to be drained, leading to significant discomfort for the patient.

SUMMARY OF THE INVENTION

Thus, it is a first aspect according to the present invention to provide a drainage valve, which allows easy finger engagement and is requiring a small amount of effort to move the valve between the open and closed positions.

It is a second aspect according to the present invention to provide a drainage valve having a simple, inexpensive and maintenance free construction while nevertheless providing a reliable seal against leakage.

It is a third aspect according to the present invention to provide a drainage valve where the patient or carer clearly is able to determine when the valve is in the open or closed position.

It is a forth aspect according to the present invention to provide a drainage valve having a design, which prevents inadvertent closure of the valve.

The novel and unique features whereby these and further aspects are achieved according to the invention is the fact that the valve member is configured such that when the valve member is moved from the closed position to an open position by rotating the operating lever at a first rotating angle α of between about 2 to about 80 degrees relative to the flow direction in the valve housing.

Thereby is obtained a drainage valve, in which patients having an extremely limited dexterity will only need to rotate the operating lever a few degrees before a flow path is such that drainage can begin.

In the context of the present invention "an open positions" means any position, which will allow a liquid to flow through the valve, i.e. the term includes both partly and completely opened positions.

It is preferred that the valve is arranged such that the flow path though the valve housings increases as the lever is rotated from the about 2 degrees towards the 80 degrees, such that the valve is only slightly opened at e.g. a 4 degrees rotation and fully opened at a 80 degrees rotation. Such a preferred embodiment will ensure that drainage of the fluid can to be drained through the valve will begin as soon as the valve is at least partly opened. Furthermore, this embodiment provides the user with the advantage that he or she is able to decide the flow rate though the valve. If a low flow rate is desired or if the urine bag only requires drainage of a low volume the operation can be rotated a few degrees, whereas if a high flow rate is desired, then the user can rotate the operation valve about 80 degrees, providing a completely opened valve having a clear flow path though the valve housing.

The valve member is preferably connected to the operating lever by means of a connection piece, which is adapted to have a close fit with the valve housing. Preferably both the valve housing and the connection piece have a mainly cylindrical shape and are arranged for providing a liquid tight fit and ease of rotation. This is e.g. obtained when the connection piece extend at least partly into the valve housing, without obstructing the flow path though the valve housing, and has a cylindrical shape that fits tightly in the cylindrical valve housing. When the connection piece has such a configuration and size the connection piece will also assist in ensuring that when the operation lever is rotated, said rotation will have an increase lateral stability by eliminating large lateral loads provided on the valve.

As the operating lever has to be rotated significantly less than the conventional drainage valves, less force has to be applied to the rotation lever than hitherto known making the drainage valve according to the invention easy to operate with a single hand, even by patients having poor dexterity. This also ensures that the known problems with opening the prior art drainage valve e.g. during a temporary emptying of a collection bag during the day, is eliminated.

The present invention relates to a drainage valve, which is particularly suitable for use together with "collection bags" for medical applications. As used herein, the term "collection bags" includes urinary bags, ileostomy bags, ureterostomy bags and the like, such as fistula bags. The invention is described herein primarily with reference to use with a urine collection bag, but it is understood that the valve according to the invention also is beneficial in any other applications which require drainage of a fluid from a reservoir or bag.

The fact that the drainage valve is opened by a slight rotation, of between about 2 and about 80 degrees, also ensures that the necessary force to reclose the valve after drainage of bodily fluids, is less than previously known, ensuring that the valve easily can be opened and closed repeatedly.

Since the drainage valve further prevents inadvertent discharge of the collected bodily fluids, a clean, efficient and fast way of drainage is provided while at the same time preventing any spillage or dripping of the bodily fluid prior to drainage.

The size of the valve member is preferably such that it covers the inlet and/or outlet opening in the valve housing, and will be removed at least partly from one of openings when the operating lever is rotated the first rotation angle of between 2 and 80 degrees.

The lever will in the open position protrude from the valve, making this configuration particularly suited for e.g. a drainage valve attached to a leg-mounted urine bag worn by an ambulatory patient under clothing since the operating lever is merely opened for periodic drainage and is mostly in the closed, non-protruding, position in which it does not become attached to the clothing.

Furthermore, the protruding operating lever also provides a clear indication that the valve is in the open position and thus acts as a reminder to the patient or carer to reclose the valve before leaving the drainage point.

However, even though a slightly protruding operating lever will have some advantages for some applications of the valve, it is an advantage if the valve also can be placed in an open position when the operating lever is not protruding from the valve, e.g. when the lever is substantially parallel with the flow direction in the valve or when the operation lever flushes with one or more elements attached to the inlet or outlet opening of the valve housing, e.g. pipes or flexible tubes, in the open position. This is preferably already the situation when the drainage valve is in the closed position, however this is also relevant when the valve is to be used for drainage in longer periods, for example in drainage systems connected to bedside storage bags and especially in systems for overnight use and for bedridden patients, a protruding lever will risk becoming attached to the bedclothes, causing inadvertent closure of the valve or providing discomfort to the patient.

It is therefore an advantage that the drainage valve according to the invention is arranged to remain in an open position during a continued rotation of the operating lever, i.e. that the valve remains in the open position after the first rotation of between about 2 to about 80 degrees in e.g. a clockwise rotation and during a continued clockwise rotation where the operating lever is subjected to an second continued rotation until the lever becomes substantially parallel with the flow direction of the fluid through the valve or when the operation lever flushes with one or more elements attached to the inlet or outlet opening of the valve housing.

Thus, the valve according to the invention preferably has a design in which the operating lever can be rotated between a closed position where the lever is substantially parallel with the flow path in the valve though an operating angle of e.g. 180 degrees. From the closed position, a first rotation of the operating lever of between 2 and 80 degrees relative to the flow direction in the valve housing, will open the valve. If the rotation of the operation lever is continued in e.g. the clockwise rotation though the remaining of the operating angle, the valve will remain open but the lever will be placed in a position where it again is substantially parallel with the flow direction or when the operation lever flushes with one or more elements attached to the inlet or outlet opening of the valve housing, ensuring that the lever cannot become entangled with e.g. the clothing. The valve according to the invention can therefore be placed in both an open and closed position where the operating lever does not protrude in any way from the valve.

With this arrangement a urine bag wearer is able to lie much more comfortably at night, when the drainage valve is open for draining. In addition, the accidental closure of the valve due to movement of the patient is less likely.

It must be understood that the operating angle depends on the design of e.g. the valve housing and the lever. However, in order to provide a valve where the operation lever is not protruding from the valve, it is preferred that the operating angle is not less than 140 degrees as the inventors have found that lower operation angle have a tendency not to place the operating lever sufficiently aliened with the flow direction therefore preventing the entanglement of the lever with the surrounding obstacles, thereby preventing that the valve is either accidentally opened or closed.

In order to obtain a valve where as little force as possible needs to be applied to the operating lever, it is preferably that the first rotation is between about 4 degrees to about 70 degrees, preferably between about 5 and about 60 degrees as this has proven to provide an especially simple and convenient drainage valve to be used by patients having a limited dexterity.

In a preferred embodiment the second rotating angle β is divided into two sub-rotation angles β1 and β2, where β1 following directly after the first rotation angle α. In this embodiment the valve member is arranged for closing the flow path through the valve housing during the rotation angle β1 and arranged for opening the flow path through the valve housing in the rotation angle β2. This embodiment provides a valve, which can be temporary closed by only rotating the operation lever a few additional degrees. This means that when the valve member has been rotated a first rotation angle of e.g. 60 degrees relative to the flow direction in the valve housing and is in a completely open position, a few additional degrees of rotation of e.g. 15-30 ensures that the valve can be closed, thereby preventing that the user has to rotate the operation e.g. the degrees counter clockwise for closing the valve. This embodiment therefore provides a very convenient and efficient way of interrupting the drainage of the fluid thought the valve for a short period of time.

The collected bodily fluids can be discharged directly from the outlet opening in the valve housing, however it is preferred that a small outlet pipe or tube is connected to the outlet opening as this will help to control the direction of the fluid during drainage. However, as the valve can drain the fluid directly into a urine collection system using the valve according to the invention does not require that a substantial length of tubing with a freely movable end be used in conjunction with the drainage valve. Thus, the possibility of such tubing springing back to its straight configuration and flicking e.g. residual urine on the patient or attending medical personnel is eliminated. Said tube or pipe can conveniently also be used to attach the collection system to a larger storage bag for continued draining during the night.

The valve housing preferably has inlet and outlet tubes or pipes respectively attached or connected to the housings inlet and outlet openings. Such tubes or pipes, provides the benefit that the temporary collection bag or night bag easily can be attached to the valve. The outlet pipe can in a preferred embodiment be designed in order to provide a convenient drainage tube in the situations where the patient would like to empty the bag during the day, thereby preventing any spillage or contamination of the surroundings. However, in other embodiments a disposable unit comprising collection bag and valve can be welded together, eliminating the need for e.g. an attachment means.

It is to be understood that the operating lever preferably is reversible rotatable, ensuring that the valve can be opened and closed several times before the valve is discharged, and the lever can be rotated clockwise and counter clockwise.

In a preferred embodiment the movable valve member within the valve housing is designed to provide a liquid tight seal against either the inlet or outlet opening of the valve housing, thereby providing a simple and efficient way of preventing liquid to flow though the valve.

This can in an especially simple embodiment be effectuated when the valve member comprises a contact surface that is complementary to the inner surface of the valve housing, at least when the valve member obstructs the liquid flow through the valve. However, in an especially simple and inexpensive embodiment the contact surface of the valve member will during the entire operating angle rotation be in contact with the inner surface of the valve housing. Such an embodiment can e.g. be obtained when the valve member comprises a curved plate, having a mainly cylindrical shape complementary to a cylindrical shape of the valve housing. The size of the plate is preferably such that is covers the inlet and/or outlet opening in the valve housing, but not larger than it will be removed at least partly from one of the openings when the operating lever is rotated the first rotation angle of between 2 and 80 degrees.

It is preferred that the valve member only has an extension should preferably be the design of the valve member, the In all cases it is an advantage if the inner surface of the valve housing and the contact surface of the valve member have a close fit, desirably an interference fit, with each other as such closely similar surface shapes assist in providing a leak-tight fit while permitting ease of rotation.

As previously mentioned a high proportion of patients requiring urine drainage catheters have limited manual dexterity such that they find it difficult to operate an associated drainage valve. In order to facilitate an ergonomic handling of the valve according to the invention the operating lever can preferably include at least one angled or curved portion at its outer end, i.e. the end remote from the valve member, so as to assist the user in placing one or two fingers or an implement, such as a metal spatula or other instrument, on or under the lever. If desired the tab can also include as a further aid to help rotating the lever, a slot or orifice to receive such an implement.

In order to assist the patient or carer, the valve in a preferred embodiment according to the invention comprises means for indicating when the valve is in either the open or closed position.

In this respect the valve member can comprise a projection arranged for engaging a stop attached to the inner surface of the valve housing when the valve is completely opened, i.e. when the operating lever has been rotated the less than 80 degrees, e.g. the preferred 60 degrees.

When the projection engages said stop during the rotating movement of the operating lever, the rotation will be slightly effected and/or partly haltered, and even though the engagement only will provide a minor disturbance in the rotation, the user will easily feel said disturbance, thereby knowing that the operating lever has been rotated sufficient to ensure that the valve according to the invention is fully opened. The patient can then decide if the valve is to be e.g. placed in said position e.g. if it is only an intermediate drainage of the collections bag is desired or alternatively continue the rotation during the operating angle until the operating lever is placed in a non-protruding way e.g. substantially parallel to the flow direction, and where the valve is in the open position.

The operating lever is preferably aligned in a common or parallel plane perpendicular to the axis of rotation of the valve member. This not only assists in easy manipulation of the lever but also offers the advantage of permitting one surface to face the user when the valve is in the open position and when the lever is either substantially parallel with the flow direction or flushes with one or more elements attached to the inlet opening of the valve housing, and a different surface when the valve is in the closed position.

This also makes it possible to place distinguishable markings on the different surfaces of the operating lever, for example placing on one surface the word "open", a first colour or surface structure and on the other surface the word "closed" or a different colour or surface structure. Using e.g. a surface structure also have the advantage that patients having an impaired eyesight can use their tactile senses, e.g. if the patient during the night will ensure if that the valve is open, he or she can simply feel the structure of the operating levers surface in order to obtain certainty, thereby eliminating the need for switching the light on.

For reasons of hygiene the valve according to the invention only needs to have a relatively short service life before disposal and thus should be of simple and inexpensive construction while nevertheless providing a reliable seal against leakage.

In a preferred embodiment the valve member and operation lever constitutes a first unit and the valve housing a second unit. Thereby is provided a simple, inexpensive and essentially maintenance free drainage valve. In this respect it is preferred that the first and second unit easily can be assembled e.g. by means of a snap fit. Such snaps fits are well known for the person skilled in the art and will therefore not be discussed in further details in this application.

The valve is preferably made from inexpensive materials, which are capable of being precision engineered. Preferably both the valve housing, valve member and operation lever are plastics mouldings. Metals such as stainless steel and aluminium are also well suited but tend to be expensive compared with the plastics alternatives.

In any case it is preferred that the valve is made of a hypoallergenic material that is non-reactive with the patient's tissue. Suitable plastics materials for the housing include polyvinyl chloride, acrylonitrile butadiene styrene, polypropylene or similar plastics.

The valve according to the invention not only has a simple and inexpensive construction, but also has a simple and user-friendly design, making it extremely easy to operate with a single hand ensuring that the valve can be unassisted used in privacy.

BRIEF DESCRIPTION OF THE DRAWINGS

The invention will be explained in greater detail below, describing only exemplary embodiments of the irrigation device with reference to the drawing, in which.

DETAILED DESCRIPTION OF THE INVENTION

The invention is described below with the assumption that the drainage valve according to the present invention is used in combination with a urine collection system. Said valve is preferably located in the bottom of a urine collection bag, which is connected to a urine catheter by flexible tubing. However, this assumption is not to be construed as limiting, and the valve can just as easily be used in other collection or drainage systems and be placed at different locations in the relevant system.

Figure 1:
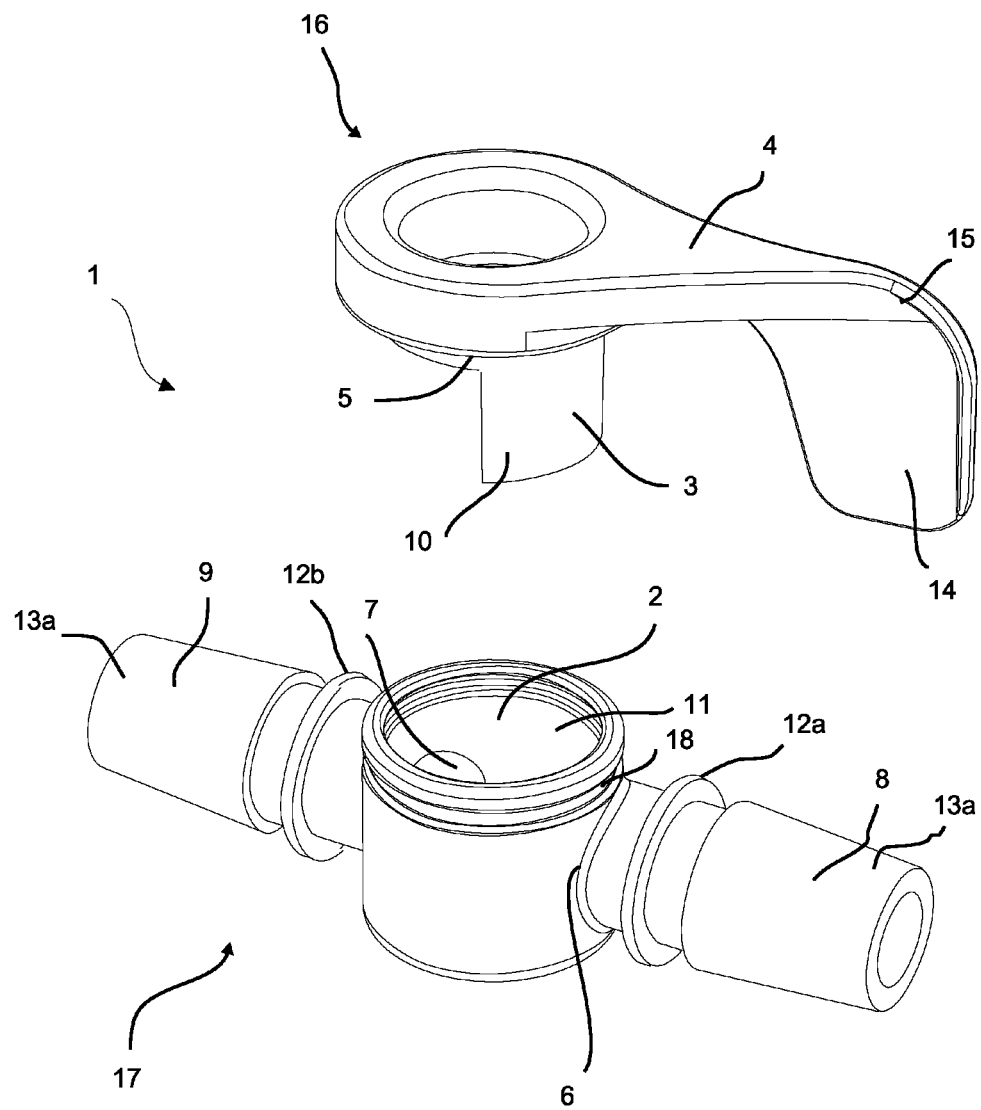
FIG. 1 shows an exploded view of a preferred embodiment of a drainage valve according to the present invention.

FIG. 1 shows an exploded view of the drainage valve 1 according to the invention. Said valve 1 consist basically of a valve housing 2, a valve member 3 and an operating lever 4 connected to the valve member 3 via a cylindrical connection piece 5. The valve housing comprises an inlet opening inlet 6 and an outlet opening 7 extending in opposite directions from the valve housing 2. An inlet pipe 8 is connected to the inlet opening 6 and an outlet pipe 9 is connected to the outlet opening 7.

The valve member 3 consists of a plate having a contact surface 10 complementary to the inner surface 11 of the valve housing 2, thereby ensuring that the contact surface 10 of the valve member 3 will be in contact with the inner surface 11 of the valve housing 2 during rotation of the operation lever 4 through any degree of an operation angle χ.

The cylindrical connection piece 5 has a close fit with the inner surface 11 of the valve housing 2 providing both a liquid tight connection and ease of rotation. When the valve 1 is assembled, the connection piece 5 will extend at least partly into the valve housing 2 without obstructing the flow path though the valve housing 2, thereby ensuring that when the operation lever 4 is rotated, said rotation will have an increase lateral stability by eliminating lateral loads provided during the users handling of the lever 4.

The inlet and outlet pipes 8, 9 are each designed for being able to securely fasten the valve 1 to the collection system. The inlet pipe 8 is can e.g. be either directly attached to a cathether or via a length of flexible tubing. Furthermore, the outlet pipe 9 can be used directly for drainage purposes, or via additional flexible tubing be connected to a larger collection bag for overnight draining purposes.

In any case, both the inlet 8 and the outlet pipe 9 are designed for providing a liquid tight seal between the pipes 8, 9 and the flexible tubing and hold the flexible tubing securely in place. In this respect each pipe 8,9 has a projection 12a,12b severing as a retainer and/or stop for the flexible tubing and a tapered sleeve 13a,13b at its proximal end, i.e. the end of the pipe 8,9 furthest away from the valve housing 2.

The tapered sleeve 13a,13b not only assist in securing the flexible tubing to the relevant pipes 8,9, but also ensures that a liquid tight fit can be provided with different diameters of the flexible tubing, thereby making the valve 1 according to the invention more flexible in use in different applications.

The operating lever 4 includes a handling portion 14 at its outer end 15 i.e. at the end remote from the valve member 3, to assist the user in rotating the operation lever 4. This is especially relevant since a high proportion of patients requiring urine drainage catheters have limited manual dexterity.

In order to help the patient or carer in determining when the valve 1 is in either the open or closed position, the valve member 3 will engaging a first stop (not shown) attached to the inner surface 11 of the valve housing 2, when the valve 1 is completely opened, i.e. when the operating lever has been rotated through the first operation angle α.

Figure 2:
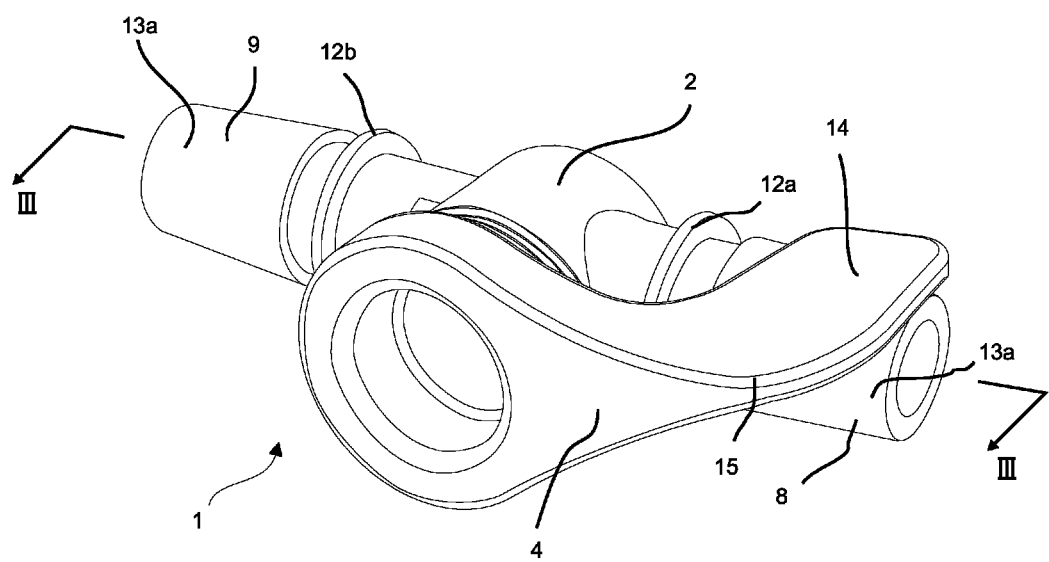
FIG. 2 shows the valve according to the invention in an assembled state.

In the embodiment shown, the valve member 3, operation lever 4 and connection piece 5, constitutes a first unit 16 and the valve housing 2, inlet and outlet pipes 8,9 constitute a second unit 17. These units can be e.g. moulded individually ensuring a simple, inexpensive and essentially maintenance free drainage valve 1 can be obtained. As is evident from FIG. 1, the valve housing 2 of the second unit 17 has a recess 18 designed to fit a circumferical corresponding projection (not shown) on the first unit 16, thereby providing a snap-fit for assembling the two units 16,17. The assembled valve is shown in FIG. 2.

The operation of the valve will be discussed with reference to the FIGS. 3 and 4 as these figures shows the drainage valve according to the invention in different perspectives and positions.

Figure 3A:
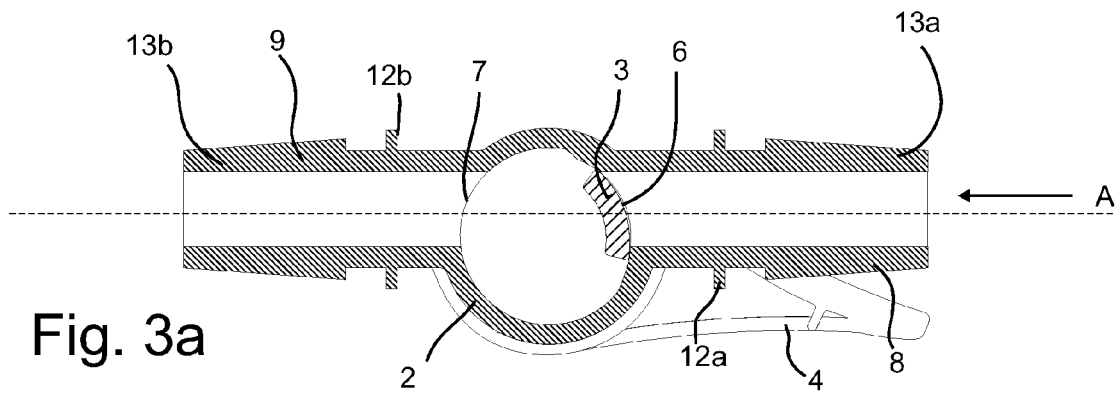
FIG. 3 shows a sectional view taken alone the lines III in FIG. 2 in the following positions, wherein the valve in FIG. 3a is in a closed position, in FIG. 3b the valve is in an open position after rotation of the operation lever in a first operation angle, and in FIG. 3c the valve is in an open position after the operation lever has been rotated a second operation angle.
Figure 4A:
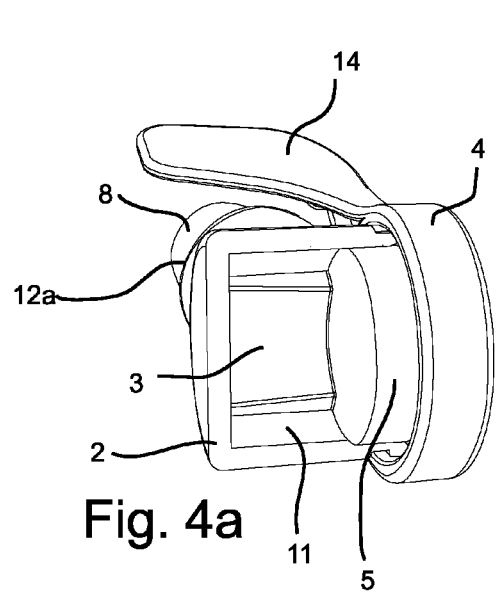
FIG. 4 is an open perspective view of the valve according to the invention wherein the valve in FIG. 4a is in a closed position, in FIG. 4b the valve is in an open position after rotation of the operation lever in a first operation angle, and in FIG. 4c the valve is in an open position after the operation lever has been rotated a second operation angle.

FIGS. 3a and 4a shows the valve 1 in a closed position, and as shown in e.g. FIG. 3a the operating lever 4 flushes with the inlet pipe 8 thereby ensuring that the operation lever 4 cannot become entangled with e.g. the clothing of the patient. The flow direction is indicated with arrow A In said closed position the valve member 3 will, as seen in FIGS. 3a and 4a mechanically obstruct the flow of the liquid, as the inner surface 11 of the valve housing 2 and the contact surface 10 of the valve member 3 have a close fit with each other, thereby ensuring a leak-tight fit while permitting ease of rotation.

When the user intends to drain liquid from the urine collection bag he or she simply has to rotate the operation lever 4 a few degrees before the liquid starts to drain. This is due to the fact that the operation lever 4 is attached to the valve member 3 via the cylindrical connection piece 5, and a rotation of the lever 4 will therefore rotate the valve member 3 accordingly.

Figure 3B:
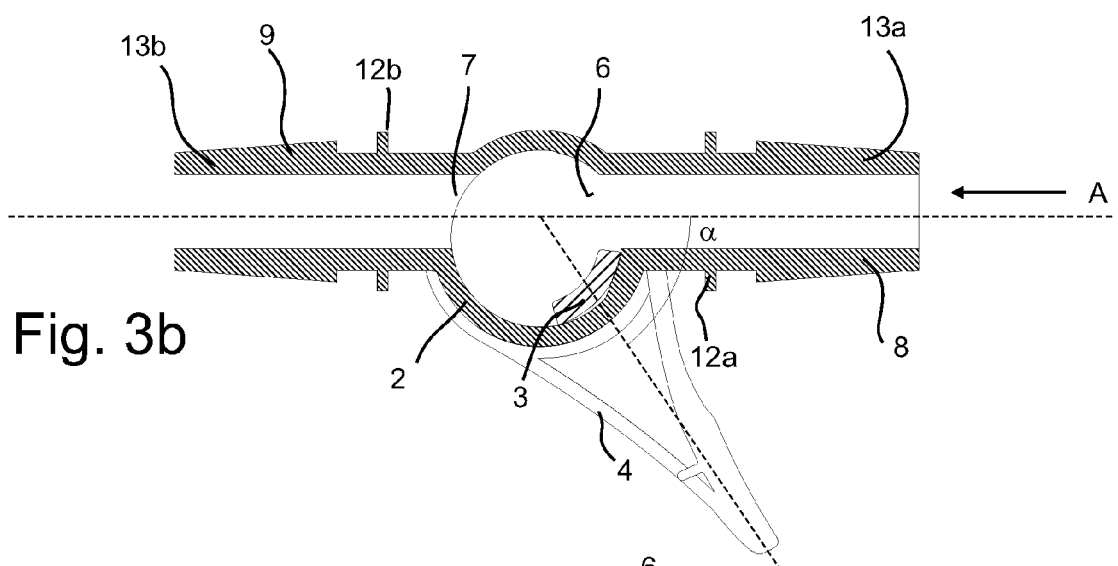
Figure 4B:
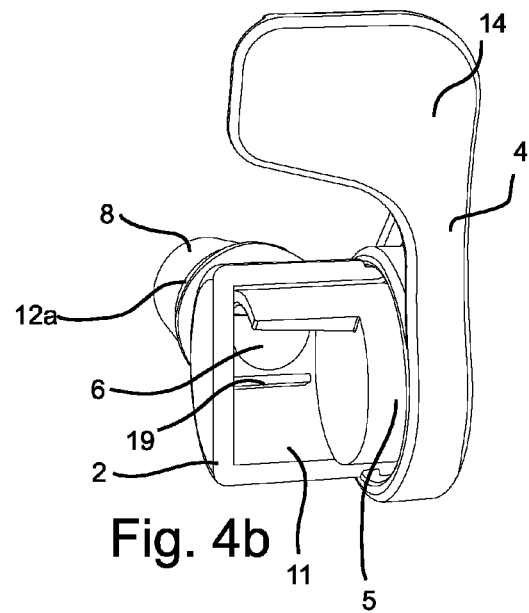

When the lever is rotated a first operating angle α of between 2 and 80 degrees, the valve member 3 is removed from both the inlet opening 6 and outlet opening 7, providing a flow path for the liquid in the valve housing 2. This flow path is seen in FIGS. 3b and 4b.

The size of the valve member 3 (plate) is such that is completely covers the inlet opening 6 in the valve housing 2 in the closed position. However the valve member only needs to extend a few millimeters beyond the inlet opening 6, such that when the operation lever 4 is rotated in the first rotation angle α, the valve member 3 will continuously be removed from the inlet opening providing an increasing flow path though the valve housing 2. As an example can be mentioned that when the operation lever 4 has been rotated e.g. 5 degrees the valve member 3 is slightly removed from the inlet opening 6, when the lever 4 is rotated 30 degrees the inlet opening 6 is half covered by the valve member 3, and when a 60 degrees rotation is completed the valve member 3 is completely removed from the inlet opening 6.

After the operating lever 4 has been rotated the first rotation angle α, said lever 4 protrudes somewhat from the valve 1. However, this protruding lever 4 has the advantage that the user has a clear indicating that the valve 1 is opened. This protruding lever 4 is therefore particularly convenient when the drainage has to be completed fast and efficient, as little force has to be applied to the operation lever 4, for both opening and closing purposes.

Figure 3C:
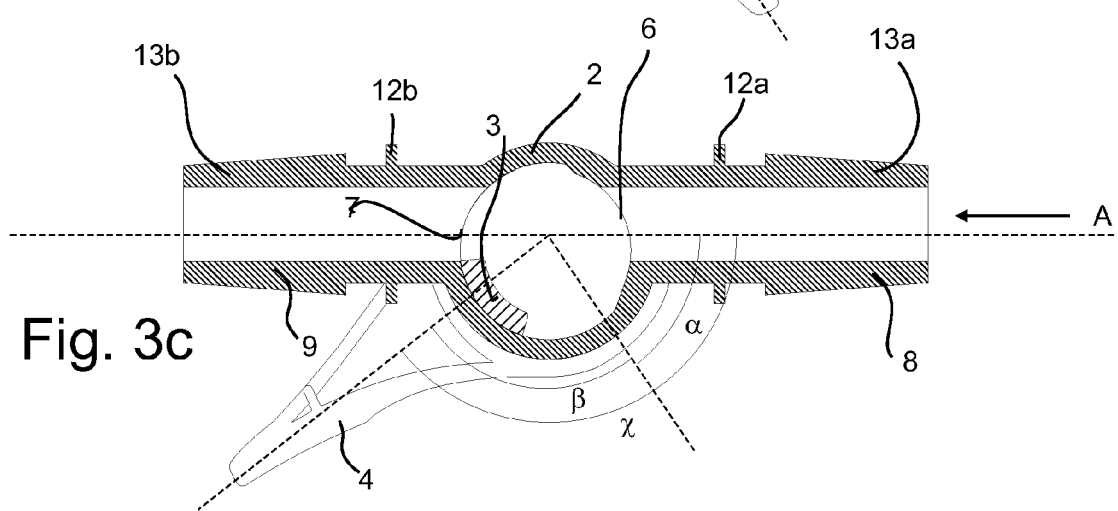

However, when the valve 1 is to be used for drainage for longer periods, for example in drainage systems connected to bedside storage bags and especially in systems for overnight use and for bedridden patients, the operating lever 4 can be subjected to a second continued rotation of an angle β as shown in FIG. 3c which will continue until the lever substantially flushes with the outlet pipe 9.

The rotating of the operating lever 4 through both the first rotation angle α and the second rotation angle β, provides an operation angle χ, see FIG. 3c—which is the sum of the first and second rotation angle.

As is evident from FIG. 3 the inlet opening 6 and outlet opening 7 is not placed directly in the middle of the valve housing. This specific construction not only ensures that the operating lever 4 has a larger operation angle but also that the lever 4 can flush with e.g. the inlet and/or outlet pipes 8,9 without and still not project from the complete valve.

In the embodiment shown in FIGS. 1-5 the first rotation angle α is about 60 degrees and the second operation angle β is about 90 degrees, giving an is operating angle χ of about 150 degrees. As seen in both FIGS. 4c and 5c the valve member 3 will not block or in any way obstruct the flow path through the valve housing 2 during the rotation angle β.

As is evident from FIG. 3c the valve 1 will remain open when the lever 4 is placed in a position where it flushes with the outlet pipe 9, ensuring that the lever 4 cannot become entangled with e.g. the clothing. The valve according to the invention can therefore be placed in both an open and closed position where the operating lever 4 does not protrude from the valve 1. With this arrangement a urine bag wearer is able to lie much more comfortably at night, when the drainage valve is open for draining. In addition, the accidental closure of the valve due to movement of the patient is less likely.

As previously described the valve member 3 will engaging a first stop (not shown) attached to the inner surface 11 of the valve housing 2, when the valve 1 is completely opened, i.e. when the operating lever has been rotated through the first operation angle α, thereby helping the patient or carer in determining when the valve 1 has reached an open position.

Figure 4C:
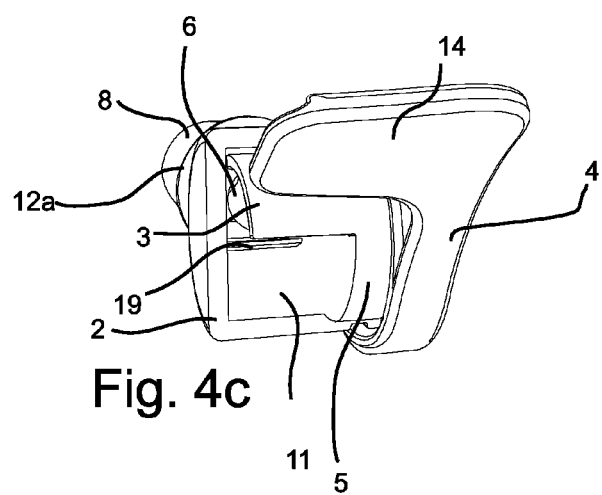

Similar can a second stop 19, shown in FIGS. 4b and 4c will engage the valve member 3 when the valve is closed, ensuring that the valve member cannot be rotated any further.

Figure 5:
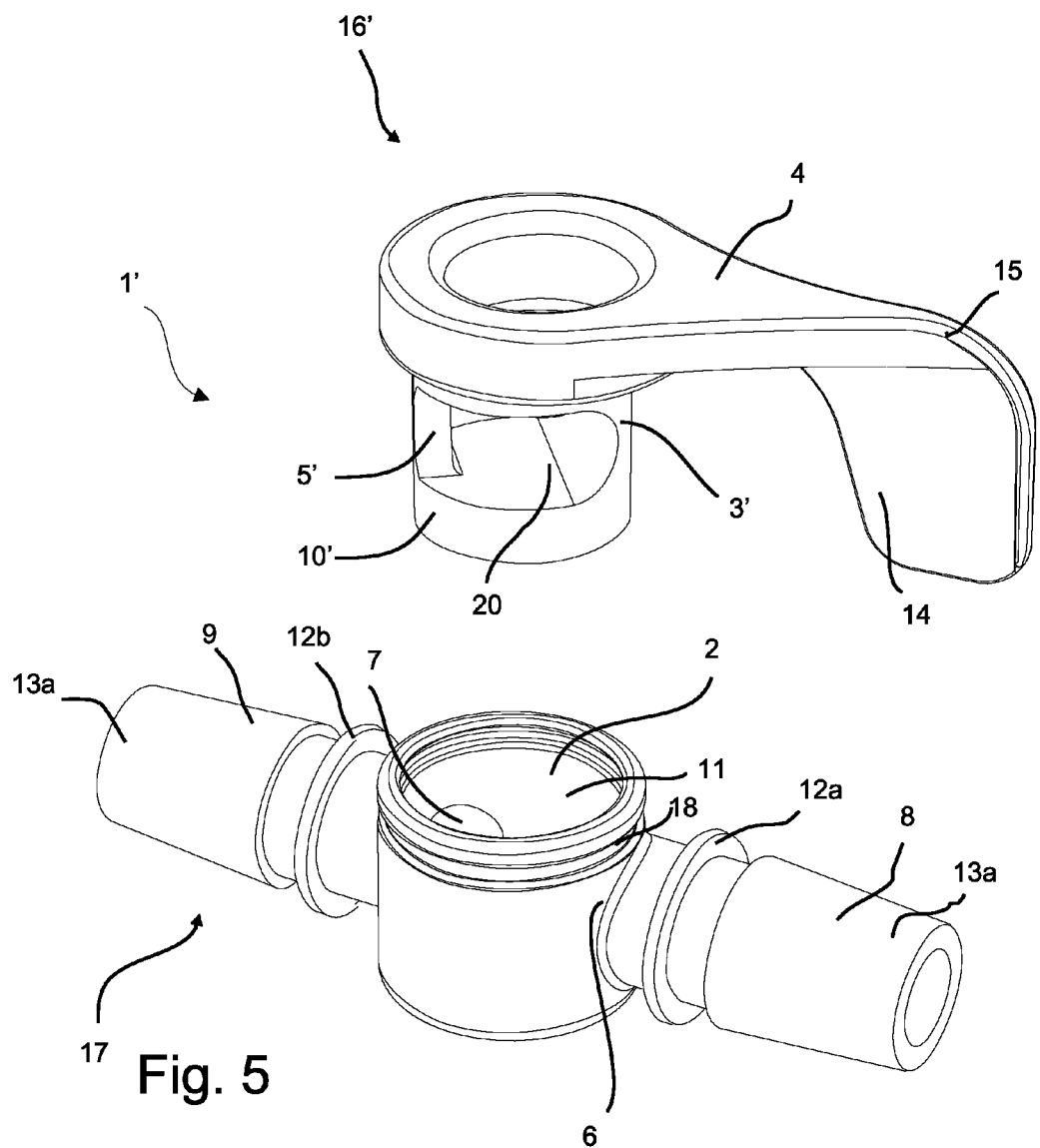
FIG. 5 shows a second embodiment of the valve according to the invention.

In FIG. 5 is shown a second embodiment 1' of the valve according to the invention. Similar reference number will be used for identical parts. The second embodiment comprises a second unit 17 similar to the second unit shown in FIG. 1 and a alternative first unit 16'. The first 16' and second unit 17 is constructed to be assembled via e.g. a similar snap-fit in a similar way as described in connection with FIG. 1.

In said embodiment the first unit 16' has a valve member 3' which consist of an extended cylindrical connection piece 5' having a thoroughgoing elongated hole 20 in the centre 21.

Figure 6A:
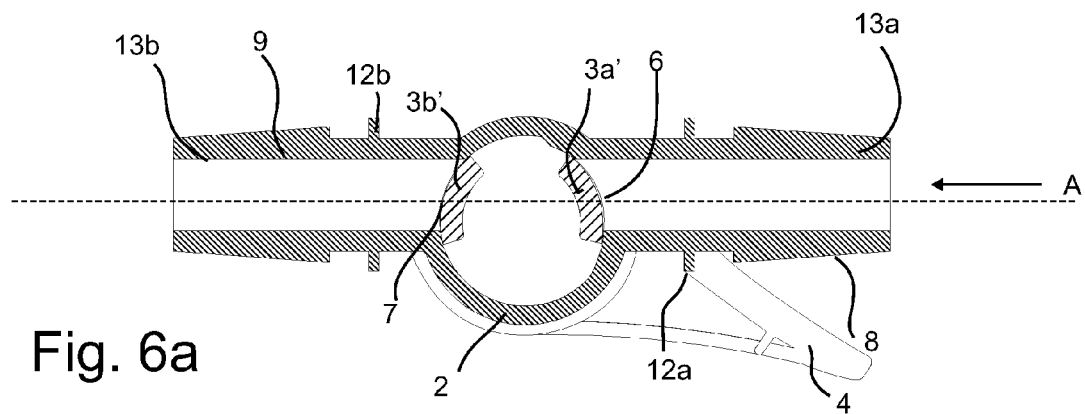
FIG. 6 shows a sectional view of the valve in FIG. 5 in the following positions, wherein the valve in FIG. 6a is in a closed position, in FIG. 6b the valve is in an open position after rotation of the operation lever in a first operation angle, in FIG. 6c the valve is in an closed position after the operation lever has been rotated in a first sub-operation angle, and FIG. 6d the valve is in an open position after rotation of the operation lever a second sub-operation angle.
Figure 6B:
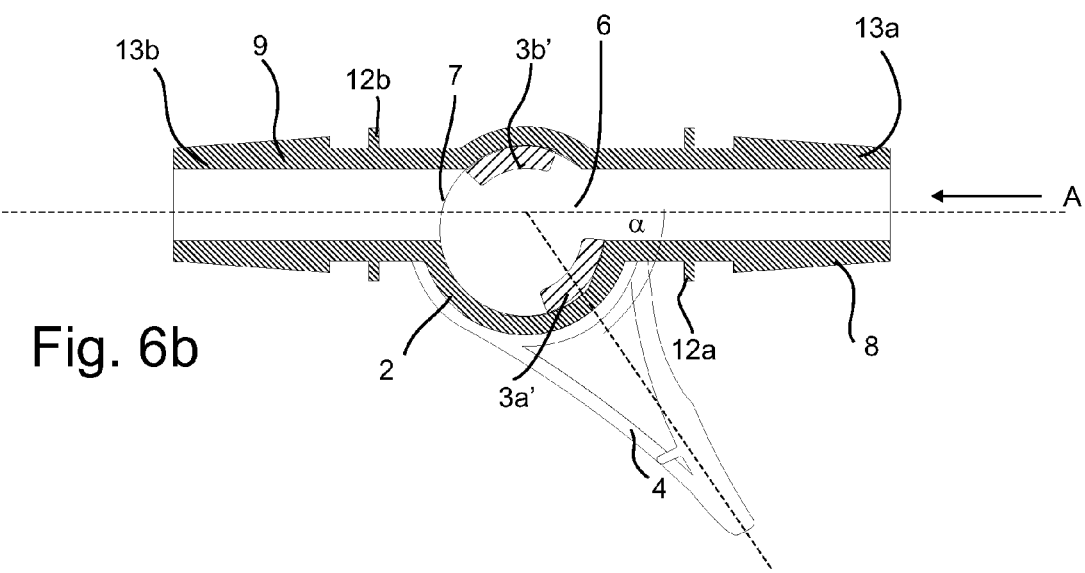
Figure 6C:
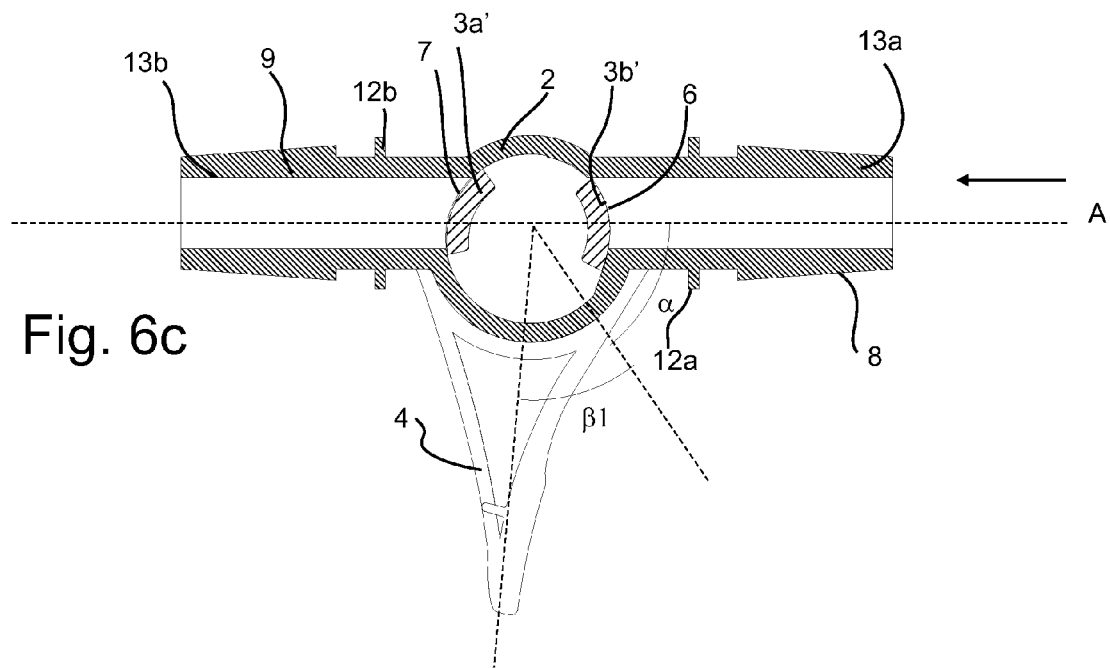
Figure 6D:
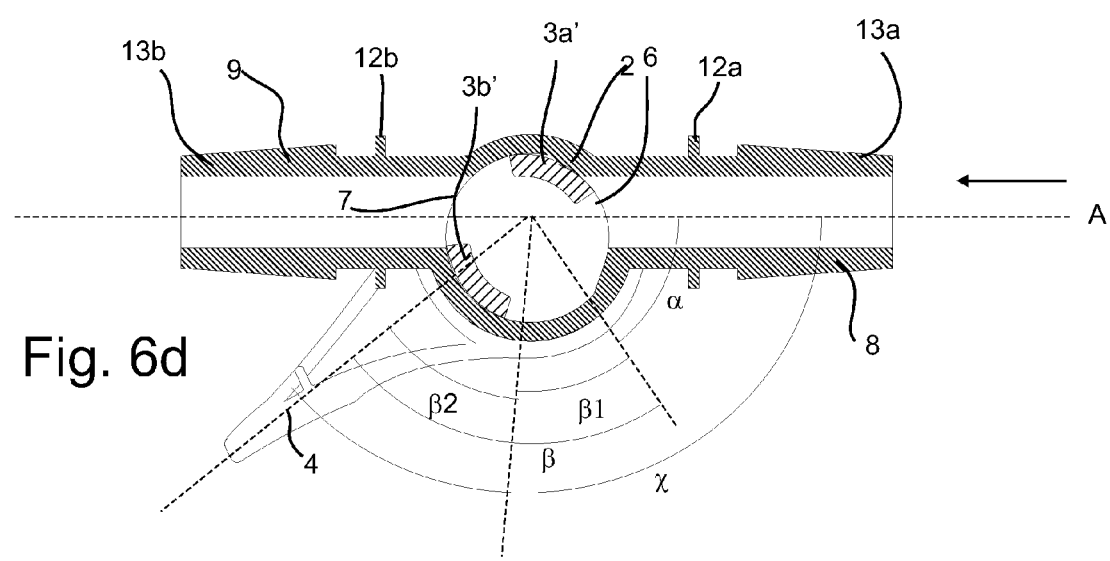

The function of the second embodiment 16' can be seen in FIGS. 6a-6d. In FIG. 6a the valve 1' is shown in a closed position, where the operating lever 4 flushes with the inlet pipe. As the valve member 3' is made of the extended cylindrical connection piece 5' having a thoroughgoing hole 20 the valve member will in the present sectional view be displaced as two parts 3a' and 3b'. In the closed position in FIG. 6a the valve member 3' will mechanically obstruct the liquid flow.

When the user intends to drain liquid from the urine collection bag he or she rotates the operation lever 4 through the first operating angle α of between 2 and 80 degrees, removing the valve member 3' from both the inlet opening 6 and outlet opening 7, providing a clear flow path for the liquid in the valve housing 2.

In the shown second embodiment the second rotating angle β is divided into two sub-rotation angles β1 and β2, where the valve member 3' will close the flow path through the valve housing 2 during the rotation angle β1, as seen in FIG. 6c and again open the flow path through the valve housing after the operation lever has been rotated an additional angle of β2. This embodiment provides a valve 1', which is temporary closed during rotation of the lever 4 after rotation of the operation angle β1, thereby ensuring that the user does not have to rotate the operation lever 4 counter clockwise for closing the valve. This embodiment therefore provides a very convenient and efficient way of interrupting the drainage of the fluid thought the valve momentarily.

The device according to the invention has a simple and inexpensive design, and can therefore be used equally well for both privately and in medical or hospital facilities where known drainage valve are too troublesome and complicated to use.

Modifications and combinations of the above principles and designs are foreseen within the scope of the present invention.

What is claimed is:

1. A drainage valve comprising an inlet opening and an outlet opening extending in opposite directions from a valve housing, a movable valve member within the housing and an operating lever connected to the valve member, the valve member movable between an open position in which the valve member is arranged to permit flow through the valve and a closed position where the valve member prevents flow through the valve, wherein the valve member is configured such that the valve member is moved from the closed position to the open position by rotating the operating lever by a first rotating angle that is between 2 degrees to 80 degrees relative to the flow direction in the valve housing, and wherein the valve has a design in which the operating lever is arranged for being rotated by a second rotating angle to a fully open position after completion of the first rotating angle, with a total of the first and second rotation angles defining an operating angle of between 140 to 180 degrees, and wherein the valve is in the fully open position after rotation of the first rotating angle and remains in the fully open position after rotation of the second rotating angle, and wherein the valve is configured such that the operating lever is generally flush with one or more elements attached to the inlet opening when the valve is in the closed position and the operating lever is generally flush with one or more elements attached to the outlet opening when the valve is in the fully open position.

2. The drainage valve according to claim 1, wherein the first rotating angle is between 4 degrees to 70 degrees.

3. The drainage valve according to claim 1, wherein the first rotating angle is between 5 and 60 degrees.

4. The drainage valve according to claim 1, wherein the valve member is connected to the operating lever by a connection piece.

5. The drainage valve according to claim 4, wherein the connection piece extends at least partly into the valve housing.

6. The drainage valve according to claim 1, wherein the valve is configured such that the valve can be placed in the closed position when the operating lever is generally parallel with the direction of flow through the valve.

7. The drainage valve according to claim 1, wherein the valve member is designed to provide a liquid tight seal against either the inlet or outlet opening of the valve housing.

8. The drainage valve according to claim 1, wherein the operating angle is about 150 degrees.

9. The drainage valve according to claim 1, wherein the valve is open during rotation of the second rotating angle.

10. The drainage valve according to claim 1, wherein the second rotating angle is divided into two sub-rotation angles and wherein the valve member is arranged for closing the flow path through the valve housing during one sub-rotation angle and arranged for opening the flow path through the valve housing in the other sub-rotation angle.

11. The drainage valve according to claim 1, wherein the valve comprises means for indicating that the valve member has been rotated by the first rotating angle.

12. The drainage valve according to claim 11, wherein the means for indicating comprises a projection on the valve member and a stop on the inside of the valve housing.

13. The drainage valve according to claim 1, wherein the valve member comprises a contact surface which is complementary to the inner surface of the valve housing.

14. The drainage valve according to claim 1, wherein the valve member comprises a curved plate having a mainly cylindrical shape complementary to a cylindrical shape of the valve housing.

15. A collection assembly for bodily fluids comprising the drainage valve according to claim 1.

16. The collection assembly according to claim 15, wherein the collection assembly is a urine collecting system.

* * * * *